US008382844B2

(12) United States Patent
Elwatidy

(10) Patent No.: US 8,382,844 B2
(45) Date of Patent: Feb. 26, 2013

(54) PRESERVATION AND RESTORATION OF CRANIAL BONE FLAPS

(75) Inventor: Sherif Elwatidy, Riyadh (SA)

(73) Assignee: King Saud University, Riyadh (SA)

( * ) Notice: Subject to any disclaimer, the term of this patent is extended or adjusted under 35 U.S.C. 154(b) by 1155 days.

(21) Appl. No.: 12/251,347

(22) Filed: Oct. 14, 2008

(65) Prior Publication Data
US 2010/0094360 A1    Apr. 15, 2010

(51) Int. Cl.
*A61F 2/02* (2006.01)
(52) U.S. Cl. ..................... 623/17.19; 422/28
(58) Field of Classification Search .......... 606/280–299; 128/898; 424/422; 422/28; 435/1.1, 1.3
See application file for complete search history.

(56) References Cited

U.S. PATENT DOCUMENTS 5,578,036 A * 11/1996 Stone et al. ................... 606/281

OTHER PUBLICATIONS

Moin et al., The Use of Frozen Autogenous Bone Flap for Cranioplasty, Dec. 2005, Journal of Research in Medical Sciences, vol. 10, No. 6, 395-397.*
Yamada et al., Cranioplasty Utilizing a Preserved Autogenous Bone Flap Coated with Acrylic Resin, 1980, Acta Neurochirurgica, 52, 273-280.*
Yong-Chen Por et al., Bone Generation in the Reconstruction of a Critical Size Calvarial Defect in an Experimental Model, Nov. 2007, Journal of Craniofacial Surgery, vol. 36, No. 11, 911-919.*
Prolo et al., Autogenous Skull Cranioplasty: Fresh and Preserved (Frozen), with Consideration of the Cellular Response, 1979, Neurosurgery, vol. 4, No. 1, 18-29.*
Cottagnoud et al., Vancomycin Acts Synergistically with Gentamicin against Penicillin-Resistant Pneumococci by Increasing the Intracellular Penetration of Gentamicin, Jan. 2003, Antimicrobial Agents and Chemotherapy, vol. 47, No. 1, 144-147.*
Flannery, T., et al.; "Cranioplasty: why throw the bone flap out?"; British Journal of Neurosurgery; vol. 15, No. 6; Dec. 1, 2001; pp. 518-520.
Goel, A., et al.; "Subgaleal preservation of calvarial flaps"; Surgical Neurology; vol. 44, No. 2; Aug. 1995; pp. 181-183.
Krishnan, P., et al.; "Bone flap preservation after decompressive craniectomy—Experience with 55 cases"; Neurology India; vol. 54, No. 3; 2006; pp. 291-291.
Korfali, E.; "Preservation of craniotomy bone flaps under the scalp"; Surgical Neurology; vol. 30, No. 4; Oct. 1988; pp. 269-272.
Nagayama, K., et al.; "Cranioplasty Using the Patient's Autogenous Bone Preserved by Freezing. An Examination of Post-operative Infection Rates"; Neurological Surgery; vol. 30, No. 2; 2002; pp. 165-169 (in Japanese).
Vanaclocha, V., et al.; "Use of frozen cranial vault bone allografts in the repair of extensive cranial bone defects"; Acta Neurochirurgica (Wien); vol. 139, No. 7; 1997; pp. 653-660.

* cited by examiner

Primary Examiner — Nicholas Woodall
Assistant Examiner — Melissa A Hall
(74) Attorney, Agent, or Firm — Hart IP Law and Strategies

(57) ABSTRACT

Methods are provided for preserving and restoring cranial bone flaps. In one aspect, the method to preserve a cranial bone flap includes cleaning a cranial bone flap, washing the cranial bone flap with a sterile saline solution including gentamycin, and washing the bone with a sterile saline solution including vancomycin. The cranial bone flap may be dried, wrapped, and packaged before being stored in a freezer. The fixing method may include removing the preserved cranial bone flap from a freezer and unwrapping the preserved cranial bone flap from any wrappings. A previous wound may be opened for insertion of the preserved cranial bone flap. The preserved cranial bone flap may be washed with a sterile saline solution including gentamycin and a sterile saline solution including vancomycin. The edges of the previous wound may be refreshed by nipping free margins to expose diploic spaces, and the preserved cranial bone flap may be fixed in place within the previous wound.

6 Claims, 3 Drawing Sheets

PRESERVATION AND RESTORATION OF CRANIAL BONE FLAPS

BACKGROUND

Refractory brain edema is a state of severe, progressive, and diffuse cerebral edema that causes rapid clinical deterioration, and does not generally respond to aggressive medical treatment. Refractory brain edema is usually seen after severe head injury, subarachnoid hemorrhage due to ruptured cerebral aneurysms, extensive brain infarction, and sometimes after excision of brain tumors. Despite advances in understanding, monitoring, and treatment, the outcome of patients with refractory brain edema remains poor with substantial mortality, severe and moderate disability rates, and corresponding low rates of successful outcomes.

The concept of wide bone removal for treatment of intracranial hypertension has been recognized since the nineteenth century. Different types of decompressive craniectomy have been described, including unilateral or bilateral frontal and subtemporal decompression and circumferential hemicraniectomy. Recently, bifrontal decompressive craniotomy has been used at increasing rates to treat refractory brain edema. Reasons for the increased use of bifrontal decompressive craniotomy include: 1) quickly lowers intracranial pressure to normal levels; 2) adds a vector of expansion to both cerebral hemispheres that may relieve subfalcine and transtentorial brain herniation; 3) quickly improves the partial pressure of brain tissue oxygen; 4) allows exploration of the subdural space on both sides of the cranium; and 5) allows quick tapering of the medical treatment (hypothermia, barbiturates, osmotic diuretics, ventriculostomy, prolonged hyperventilation, and hypertonic saline) to minimize side effects.

Preservation of bone flaps in a good and viable condition after a bifrontal decompressive craniotomy represents a formidable challenge. Currently, preservation of bone flaps in a good and viable condition is only possible by keeping the bone inside the body, such as under the skin of the abdominal wall or the thigh. The large size and round shape of the forehead bone, however, may exclude these sites even after breaking the bone into smaller pieces. The reconstruction of the resulting huge skull defect from the bifrontal decompressive craniotomy may only be possible by use of the patient's own bone. Using synthetic materials, like ceramic bone and custom bone, are very expensive. Furthermore, restoration of the normal shape and contour of the forehead is difficult using synthetic materials. Ideal cranioplasty materials should have maximal biocompatibility, low cost, low incidence of complications, wide accessibility, and ease of use. Autologous bone is considered the best material for cranioplasty; however, preservation of the bone entails morbidity related to the donor area, lengthening of the surgical procedure, and limited amount of bone that can be used for grafting.

Cranioplasty following an extended decompressive craniectomy is a formidable challenge, and its complexity increases with the size of the bone defect. Re-implantation of a patient's own bone flap yields excellent cosmetic results, with short operation time and without needing extensive remodeling. Several techniques for in-vivo preservation of craniectomy bone flap currently exist. In-vivo preservation sites may include the anterior abdominal wall, the front of the thigh, and subgaleal spaces. These sites, however, are not suitable for the very large and rounded forehead bones. Alternatively, bone flaps may be preserved in a bone bank using deep freezing at temperatures of approximately −80° C. Sterilization techniques for these bone flaps may include autoclaving, gamma irradiation, ethylene oxide (EtO) gas, and/or hydrogen peroxide ($H_2O_2$). All the above methods of bone flap sterilization kill the bone and are associated with increased risk of bone resorption and infection after reimplantation into the donor patient.

SUMMARY

Methods for cranial bone flap preservation and restoration include, for example, methods for preservation and storage of craniectomy bone flaps for extended periods outside the human body and methods for fixing the preserved bone in a patient. In one aspect, a method of fixing a preserved cranial bone flap in a patient includes removing a preserved cranial bone flap from a freezer. The cranial bone flap may be preserved by cleaning a cranial bone flap, washing the cranial bone flap with a sterile saline solution comprising gentamycin, washing the cranial bone flap with a sterile saline solution comprising vancomycin, drying the cranial bone flap, wrapping the cranial bone flap, packing the cranial bone flap in one or more layers of sterile containers, and storing the cranial bone flap in a freezer. After removing the preserved cranial bone flap from a freezer, the preserved cranial bone flap may be unwrapped from any wrappings. A previous wound in a patient is opened for insertion of the preserved cranial bone flap. The preserved cranial bone flap is washed with a sterile saline solution comprising gentamycin and washed with a sterile saline solution comprising vancomycin. The previous wound may be refreshed by nipping free margins to expose diploic spaces before fixing the preserved cranial bone flap in place within the previous wound.

This Summary is provided to introduce a selection of concepts in a simplified form further described below in the detailed description. This Summary is not intended to identify key features or essential features of the claimed subject matter, nor is it intended to be used as an aid in determining the scope of the claimed subject matter. Additional features, advantages, and embodiments of the methods for preserving and restoring cranial bone flap are set forth or apparent from consideration of the following detailed description, drawings, and claims. Moreover, it is to be understood that both the foregoing Summary and the following detailed description are exemplary and intended to provide further explanation without limiting the scope of the methods for preserving and restoring cranial bone flap as claimed.

DETAILED DESCRIPTION

The methods for preservation and restoration of bone described in the following paragraphs may be safe for preservation of bone, such as, for example, large bone flaps with surface areas larger than approximately 150 $cm^2$, outside a human body. The methods may also be used for other types and sizes of bones that require preservation and storage. The methods may keep the bone viable and sterile after long periods of preservation. The methods for preservation and restoration of cranial bone flap may include a protocol for preserving a cranial bone flap removed from a patient that undergoes a decompressive craniectomy for an intractable brain edema. In certain embodiments, the cranial bone flap is preserved in a freezer at a temperature of approximately −18° C.

Figure 1:
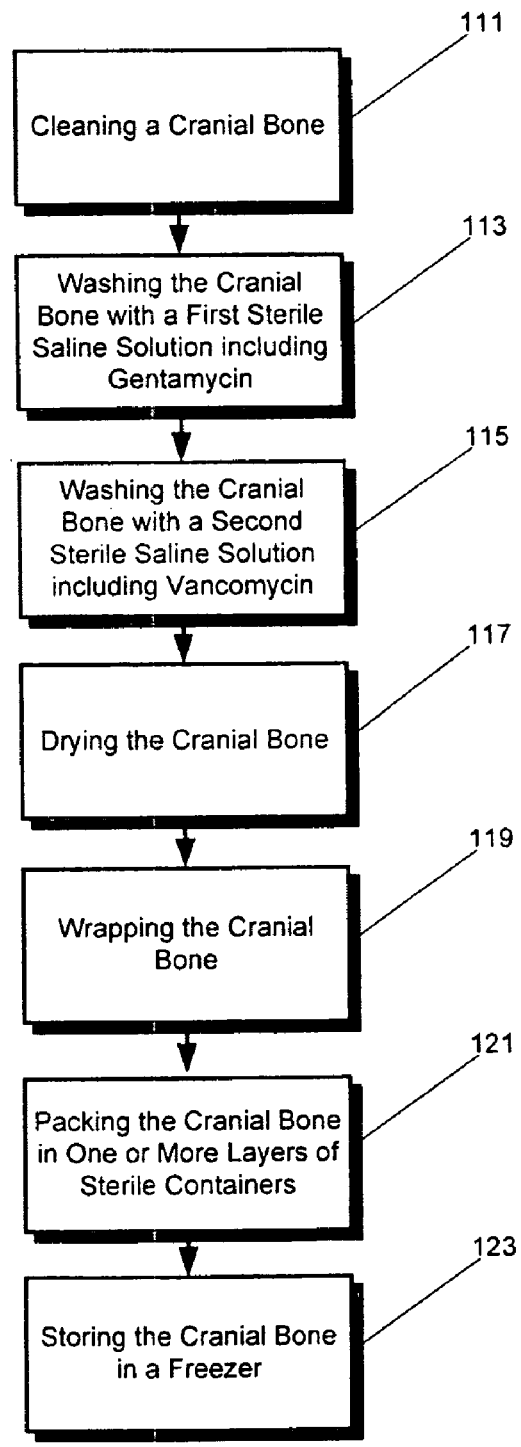
FIG. 1 shows an exemplary method for preservation of a cranial bone flap, according to one embodiment.

FIG. 1 illustrates an embodiment of a method for preservation of a cranial bone flap. In this embodiment, the cranial bone flap is prepared after bony decompression and dural release but before wound closure. The cranial bone flap may be cleaned 111. Cleaning may include removing soft tissue, bone dust, blood clots, sharp bone specules, and other undesirable materials.

In this embodiment, the bone is washed thoroughly with approximately 1 liter of a first sterile saline solution 113, the first sterile saline solution 113 including approximately 0.9% NaCl. This first sterile saline solution 113 contains approximately 80 milligrams (mg) of gentamycin per liter of solution. In another implementation, this first sterile saline solution 113 contains approximately 60 mg to 80 mg of gentamycin per liter of solution. Gentamycin is an antibiotic complex elaborated by fungi of the genus *Micromonospora*, effective against many gram-negative bacteria, especially *Pseudomonas* species, as well as certain gram-positive bacteria, especially *Staphylococcus aureus*. As with other aminoglycoside antibiotics, gentamycin is ototoxic and nephrotoxic.

In this embodiment, the bone is then washed thoroughly with approximately 1 liter of a second sterile saline solution 115, the second sterile saline solution 115 including approximately 0.9% NaCl. This second sterile saline solution 115 contains approximately 1 g of vancomycin per liter of solution. Vancomycin is a glycopeptide antibiotic used in the prophylaxis and treatment of infections caused by gram-positive bacteria.

After the washing steps, the bone may be dried 117 and wrapped 119 with, for example, dry, sterile towels or other suitable wrappings. The wrapped bones may be packed 121 in one or more layers of additional wrappings or containers. The one or more layers of wrappings or containers may preferably be two layers of sterile plastic bags. In this embodiment, the wrapped and packaged bone is stored 123 in a freezer kept at a temperature of approximately −18° C. Preferably, the packaging is tagged with the patient's name, hospital number, date of removal, and/or other desired information. The preserved bone may be stored in the freezer until needed for a procedure to fix the preserved bone in a desired position within the patient.

Figure 2:
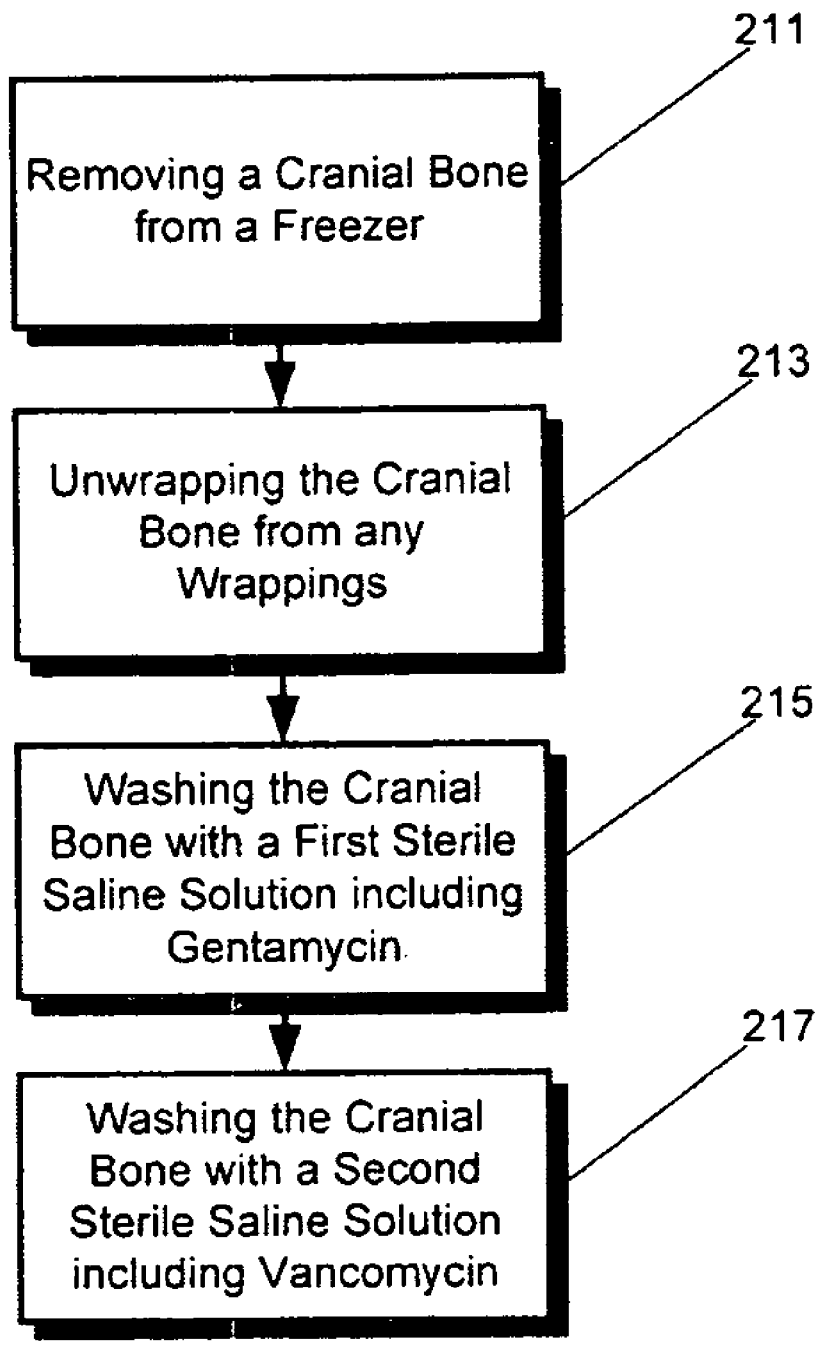
FIG. 2 shows an exemplary method for preparing a preserved cranial bone flap, according to one embodiment.

FIG. 2 illustrates an embodiment of a method for preparing a preserved cranial bone flap to be fixed in a desired position within the patient. The method of preparing the preserved bone includes, for example, the steps of removing the bone from the freezer 211 and unpacking and/or unwrapping 213 the bone using strict aseptic precautions. The strict aseptic precautions may be similar to those used in cerebrospinal fluid shunt procedures. In this embodiment, the bone is then washed thoroughly with approximately 1 liter of a first sterile saline solution 213, the first sterile saline solution 213 including approximately 0.9% NaCl. This first sterile saline solution 213 contains approximately 80 mg of gentamycin per liter of solution. The bone is then washed thoroughly with approximately 1 liter of a second sterile saline solution 215, the second sterile saline solution 215 including approximately 0.9% NaCl. This second sterile saline solution 215 contains approximately 1 g of vancomycin per liter of solution. In this embodiment, the washing steps may take place after the previous wound is opened.

Figure 3:
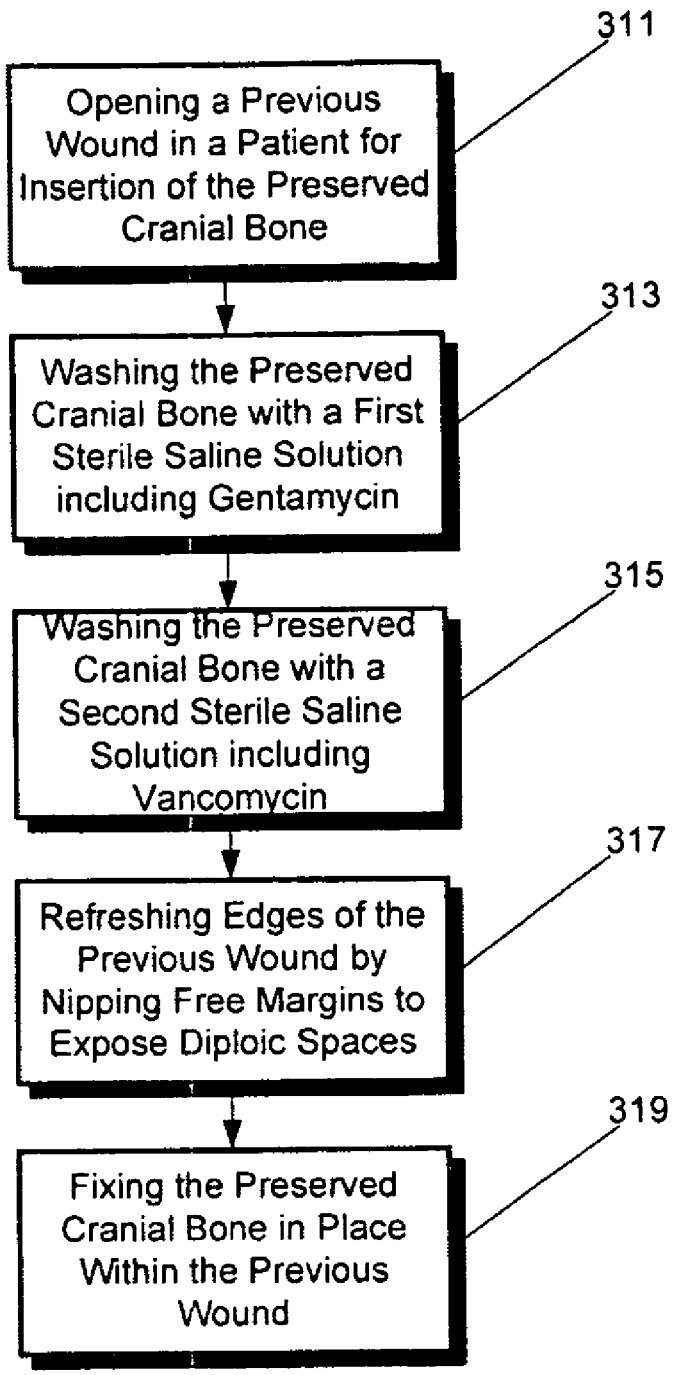
FIG. 3 shows an exemplary method of restoring a preserved cranial bone flap, according to one embodiment.

FIG. 3 illustrates an embodiment of a method for fixing a preserved cranial bone flap in a desired position within a patient. A previous wound may be opened 311. In this embodiment, the bone is then washed thoroughly with approximately 1 liter of a first sterile saline solution 313, the first sterile saline solution 313 including approximately 0.9% NaCl. This first sterile saline solution 313 contains approximately 80 mg of gentamycin per liter of solution. The bone is then washed thoroughly with approximately 1 liter of a second sterile saline solution 315, the second sterile saline solution 315 including approximately 0.9% NaCl. This second sterile saline solution 315 contains approximately 1 gram of vancomycin per liter of solution.

Edges of a previous wound are refreshed 317 by nipping using a bone nibbler. A free margin of the previous wound is nipped to expose diploic spaces. This may allow bone growth and reunion of the bone. The refreshing step may be performed after or contemporaneously with the washing steps. In this embodiment, the bone is then fixed 319 in place using titanium plates, screws, or other suitable methods of securing the bone in a desired position. After the bone is fixed, the wound is sealed. Antibiotics may be started and/or continued after surgery for approximately ten days. Plain x-rays and CT scans may be performed immediately after a cranioplasty and may be repeated after approximately six months to check bony fusions and bone thickness.

Studies were performed to evaluate the methods described above for preservation of large craniectomy bone flaps in a freezer at a temperature of approximately −18° C. for long periods of time using microbiological and histological examination. Microbiology swabs and histology specimens were taken from fourteen bone flaps and sent for microbiological and histological examinations to check both sterility and viability of the bone flaps after long periods of preservation. Microbiology and histology specimens were taken from the bone flaps just before their replacement into a patient. The dimensions of the bone flaps ranged from approximately 5×7 cm to approximately 13×25 cm, with a mean surface area of approximately 228 $cm^2$. The duration of preservation ranged from 60 days to 1,920 days, with a mean duration of 313 days.

Microbiological Methods

Microbiology swabs were taken from bone flaps before replacement and were inoculated aerobically and anaerobically on regular and enriched media with subcultures done to check the sterility of bone flaps after long periods of preservation in the freezer. None of the blood agar, MacConkey agar plates, or Robertson cooked meat media yielded any bacterial growth.

Exemplary Histopathologic Examination

Bone specimens were examined histologically to study the effect of freezing on bone viability. At the time of cranioplasty, small pieces were taken from different sides of the bone flaps and sent to the lab for decalcification, staining, and histological examination.

Exemplary Results

Fourteen bone flaps were examined histologically and microbiologically. All of the bone flaps showed no bacterial contamination. All except one bone flap, which was preserved for 1,920 days, showed viable bone. Bone flap infection was minimized.

Conclusion

The above-described exemplary embodiments of methods for preserving and restoring cranial bone flaps are presented for illustrative purposes only. While these methods for preserving and restoring cranial bone flaps are satisfied by embodiments in many different forms, it is understood that the present disclosure is to be considered as exemplary and is not intended to limit the described systems and methods to the specific embodiments illustrated and described herein. Numerous variations may be made by persons skilled in the art without departure from the spirit of this description. Moreover, features described in connection with one embodiment may be used in conjunction with other embodiments, even if not explicitly stated above. The scope of the methods for preserving and restoring cranial bone flaps will be measured by the appended claims and their equivalents. The abstract and the title are not to be construed as limiting the scope of the claims, as their purpose is to enable the appropriate authorities, as well as the general public, to quickly determine the general nature of the described systems and methods. In the claims that follow, unless the term "means" is used, none of the features or elements recited therein should be construed as means-plus-function limitations pursuant to 35 U.S.C. §112, ¶6.

The invention claimed is:

1. A method of fixing a preserved cranial bone flap in a patient, the method comprising:
   removing a preserved cranial bone flap from a freezer, wherein the cranial bone flap was preserved by cleaning a cranial bone flap, washing the cranial bone flap with a sterile saline solution comprising gentamycin, washing the cranial bone flap with a sterile solution comprising vancomycin, drying the cranial bone flap, wrapping the cranial bone flap, packing the cranial bone flap in one or more layers of sterile contains, and storing the cranial bone flap in a freezer;
   unwrapping the preserved cranial bone flap from any wrappings;
   opening a previous wound in a patient for insertion of the preserved cranial bone flap;
   washing the preserved cranial bone flap with a first sterile saline solution comprising gentamycin;
   washing the preserved cranial bone flap with a second sterile saline solution comprising vancomycin;
   refreshing edges of the previous wound by nipping free margins to expose diploic spaces; and
   fixing the preserved cranial bone flap in place with the previous wound.

2. The method of claim 1 wherein the first sterile saline solution comprising gentamycin comprises approximately 80 mg of gentamycin per 1 L of the first sterile saline solution comprising gentamycin.

3. The method of claim 1 wherein the second sterile solution comprising vancomycin comprises approximately 1 mg of vancomycin per 1 L of the second sterile saline solution comprising vancomycin.

4. The method of claim 1 wherein the freezer is kept at approximately −18° C.

5. The method of claim 1 wherein the preserved cranial bone flap is fixed using plates and screws.

6. The method of claim 1 wherein each washing uses approximately 1 L of sterile saline solution.

* * * * *